United States Patent [19]

Harandi

[11] Patent Number: 4,886,925

[45] Date of Patent: Dec. 12, 1989

[54] OLEFINS INTERCONVERSION AND ETHERIFICATION PROCESS

[76] Inventor: Mohsen N. Harandi, 12 Catbird Ct., Lawrenceville, N.J. 08648

[21] Appl. No.: 189,450

[22] Filed: May 2, 1988

[51] Int. Cl.$^4$ .......................... C07C 1/20; C07C 2/00
[52] U.S. Cl. .................................... 585/331; 585/314; 585/319; 585/322; 585/323; 585/329; 585/332; 585/731; 585/733; 585/640; 585/469; 585/408; 568/697
[58] Field of Search ............... 585/331, 314, 319, 322, 585/323, 332, 329, 731, 733, 640, 469, 408; 568/697

[56] References Cited

U.S. PATENT DOCUMENTS

| | | | |
|---|---|---|---|
| 3,931,349 | 1/1976 | Kuo | 260/668 R |
| 3,960,978 | 6/1976 | Givens et al. | 260/683.15 R |
| 4,021,502 | 5/1977 | Plank et al. | 260/683.15 R |
| 4,404,414 | 9/1983 | Penick et al. | 585/469 |
| 4,456,779 | 6/1984 | Owen et al. | 585/415 |
| 4,511,747 | 4/1985 | Wright et al. | 585/415 |
| 4,542,252 | 9/1985 | Graziani et al. | 585/640 |
| 4,544,776 | 10/1985 | Osterburg et al. | 568/697 |
| 4,603,225 | 7/1986 | Colaianne et al. | 568/697 |
| 4,684,757 | 8/1987 | Avidan et al. | 585/331 |
| 4,746,761 | 5/1988 | Avidan et al. | 585/331 |
| 4,754,078 | 6/1988 | Vora et al. | 585/331 |
| 4,761,504 | 8/1988 | Pujado | 585/331 |

FOREIGN PATENT DOCUMENTS

| | | |
|---|---|---|
| 0026041 | 1/1983 | European Pat. Off. |
| 0775838 | 4/1983 | European Pat. Off. ........... 568/697 |
| 0206594 | 12/1986 | European Pat. Off. ........... 568/697 |
| 2705538 | 8/1978 | Fed. Rep. of Germany ...... 568/699 |

Primary Examiner—H. M. S. Sneed
Assistant Examiner—Chung K. Pak
Attorney, Agent, or Firm—Alexander J. McKillop; Charles J. Speciale; Lowell G. Wise

[57] ABSTRACT

An integrated process is disclosed for the conversion of $C_2+$ normal olefins into methyl tertiaryalkyl ethers and high octane gasoline. The process combines olefins interconversion with etherification and conversion of unreacted methanol and olefins in contact with acidic, shape selective metallosilicate zeolite catalyst.

13 Claims, 1 Drawing Sheet

OLEFINS INTERCONVERSION AND ETHERIFICATION PROCESS

This invention relates to a process for the production of liquid fuels from lower olefins. The invention particularly relates to an integrated process for the production of tertiary alkyl ethers and high octane gasoline by interconversion of lower olefins and the conversion of olefins to higher hydrocarbons.

BACKGROUND OF THE INVENTION

In recent years, a major technical challenge presented to the petroleum refining industry has been the requirement to establish alternate processes for manufacturing high octane gasoline in view of the regulated requirement to eliminate lead additives as octane enhancers as well as the development of more efficient, higher compression ratio gasoline engines requiring higher octane fuel. To meet these requirements the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the economic impact on the cost of gasoline is significant. Accordingly, workers in the field have intensified their effort to discover new processes to manufacture the gasoline products required by the market place. One important focus of that research is new processes to produce high octane gasolines blended with lower aliphatic alkyl ethers as octane boosters and supplementary fuels. $C_5-C_7$ methyl alkyl ethers, especially methyl tertiary butyl ether (MTBE) and tertiary amyl methyl ether (TAME) have been found particularly useful for enhancing gasoline octane. Therefore, improvements to the processes related to the production of these ethers are matters of high importance and substantial challenge to research workers in the petroleum refining arts.

It is known that isobutylene may be reacted with methanol over an acidic catalyst to provide methyl tertiary butyl ether (MTBE) and isoamylenes may be reacted with methanol over an acidic catalyst to produce tertiary-amyl methyl ether (MTBE). In these etherification processes a problem of major importance is that methanol is not totally converted and the separation of methanol from the etherification reaction product due to the proclivity of methanol to form a very dilute azeotropic mixture with hydrocarbons and the strong solubility of methanol in both water and hydrocarbons. Due largely to these factors, the cost associated with methanol separation and recycling in the etherification reaction represents approximately 30% of the cost of the total etherification process.

In U.S. Pat. No. 4,684,757 to Avidan et al. the well-known ability of zeolite type catalyst to convert methanol to olefins is utilized by directing unreacted methanol from an etherification reaction to a zeolite catalyzed conversion reaction for conversion to olefin, thereby obviating the need to separate and recycle methanol in the etherification reaction. However, the process of Avidan et al. converts oxygenate feedstock. The process incorporates an alkylation step in one embodiment to produce alkylate as well as $C_5+$ gasoline and $C_5+$ ethers.

The process for the conversion of methanol to olefins utilized in the Avidan et al. patent is but one in a series of analogous processes based upon the catalytic capabilities of zeolites. Depending on various conditions of space velocity, temperature and pressure methanol, and lower oxygenates in general, can be converted in the presence of zeolite type catalyst to olefins which may then oligomerize to provide gasoline or distillate or be converted further to produce aromatics.

In another application of zeolite catalysis, at low pressure and high temperature light olefins can be interconverted or redistributed to produce higher olefins rich in isoalkenes.

The feasibility and adaptability of the basic chemistry of zeolite oxygenates conversion to produce useful conversion processes has been the subject of much inventive research activity. Recent developments in zeolite catalyst and hydrocarbon conversion processes have created interest in using olefinic feedstocks for producing $C_5+$ gasoline, diesel fuel, etc. In addition to the basic work derived from ZSM-Z5 type zeolite catalyst, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2-C_5$ alkenes. In U.S. Pat. Nos. 3,960,978 and 4,021,502, Plank Rosinski and Givens disclose conversion of $C_2-C_5$ olefins, alone or in admixture with paraffinic components into higher hydrocarbons over crystalline zeolites having controlled acidity. Garwood et al. have also contributed improved processing techniques to the MOGD system as in U.S. Pat. Nos. 4,150,062, 4,211,640 and 4,227,992. The conversion of olefins to gasoline using a fluidized catalyst bed is the subject of U.S. Pat. application Ser. No. 006407 to Owen, et al. The above identified disclosures are incorporated herein by reference. Under conditions of moderate reaction severity, olefins are converted to predominantly gasoline boiling range products in a modification of the MOGD process known as Mobil Olefins to Gasoline (MOG).

A well-known process for the conversion of oxygenates to gasoline is the methanol to gasoline process, known as MTG. The process is described in U.S. Pat. 3,931,349 to Kuo, U.S. Pat. 4,404,414 to Penick et al. and in the publication by C.D. Chang, Catal. Rev.-Sci. Eng., 25, 1 (1983). These references are incorporated herein in their entirety Recognizing the limiting problems of the etherification processes to produce MTBE and TAME and the potential that resides in the general area of the chemistry of oxygenate and olefin conversion with zeolites to resolve those problems, several objectives of the instant invention have been established.

First, it is an object of the present invention to provide an integrated process for the production of liquid fuel mixtures from olefin containing feedstock and lower alkyl alcohols by etherification and olefin conversion and interconversion reactions.

It is another object of the present invention to provide a process for the production of liquid fuels of enhanced octane value containing MTBE and TAME.

A further object of the instant invention is an integrated liquid fuels process wherein the etherification reaction is conducted with excess alcohol but which eliminates the need to recycle excess alcohol in the etherification reactor and unreacted paraffins and olefins are converted to aromatics.

Yet another object of the instant invention is a process employing $C_2+$ normal olefins to produce higher olefins suitable for etherification and olefin conversion feedstock.

SUMMARY OF THE INVENTION

The surprising discovery has been made that the process of interconverting lower olefins such as $C_2+$ olefins to produce higher lower olefins rich in iso-olefins can be advantageously integrated with the process to produce tertiary alkyl ethers such as methyl tertiary alkyl ether (MTBE) and methyl tertiary amyl ether (TAME) and processes to convert lower oxygenates and olefins to higher hydrocarbons. In the integrated process excess methanol used in the etherification reaction is not recovered and recycled to the etherification reaction but passed to an oxygenates and olefins or olefins and paraffins conversion zone in contact with metallosilicate zeolite catalyst for conversion to liquid fuels or aromatics. Olefins from the interconversion step or the entire interconversion reaction effluent are used as feedstock to the etherification reaction either alone or in combination with another hydrocarbon feedstream rich in iso-alkenes.

More particularly, a process has been discovered for producing liquid fuel mixtures from olefin feedstock and lower alcohols by multistage etherification, olefin interconversion and oligomerization reactions, comprising the steps of:

(a) contacting an olefinic hydrocarbon feedstock rich in $C_2+$ n-alkenes with acidic, medium pore metallosilicate particles in an olefin interconversion zone under mild olefin interconversion conditions whereby a first effluent stream comprising $C_4-C_6$ alkenes rich in iso-alkenes, a second stream comprising $C_7+$ olefinic gasoline boiling range hydrocarbons and a third stream comprising unconverted hydrocarbons is produced;

(b) reacting said first stream with a stoichiometric excess of lower aliphatic alcohols in the presence of an acid etherification catalyst under reaction conditions effective to produce a mixture of tertiary alkyl ethers;

(c) recovering a light hydrocarbon fraction containing unreacted alkenes from the reaction effluent of step (b) along with unreacted alcohol;

(d) contacting the recovered light hydrocarbon and alcohol fraction from step (c) and step (a) second and third stream with an acid oligomerization and oxygenate conversion catalyst to convert at least a portion of said unreacted alkenes and alcohol to heavier liquid hydrocarbon product, including $C_{10}+$ distillate range hydrocarbons, aromatics and/or $C_5-C_9$ gasoline boiling range hydrocarbons. Optionally, alkanes may also be converted in step (d) as well as unreacted alkenes.

DESCRIPTION OF SPECIFIC EMBODIMENTS

Figure 1:
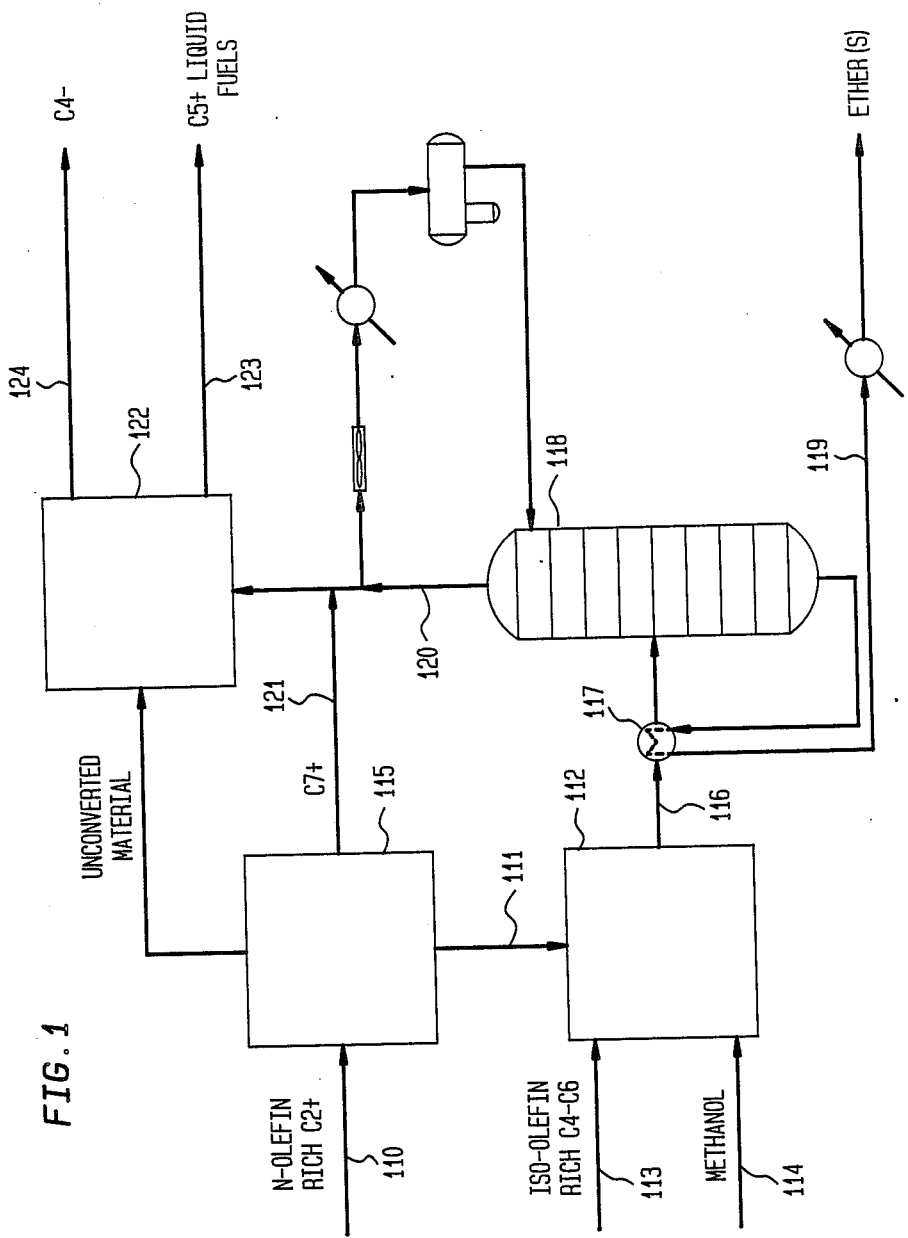
FIG. 1 is a schematic drawing of the process of the instant invention.

In the preferred embodiments of this invention methanol is reacted with a hydrocarbon feedstock containing olefins and particularly iso-olefins such as isobutene to produce methyl tertiary butyl ethers and other ethers.

Methanol may be readily obtained from coal by gasification to synthesis gas and conversion of the synthesis gas to methanol by well-established industrial processes. As an alternative, the methanol may be obtained from natural gas by other conventional processes, such as steam reforming or partial oxidation to make the intermediate syngas. Crude methanol from such processes usually contains a significant amount of water, usually in the range of 4 to 20 wt %. The etherification catalyst employed is preferably an ion exchange resin in the hydrogen form; however, any suitable acidic catalyst may be employed. Varying degrees of success are obtained with acidic solid catalysts; such as, sulfonic acid resins, phosphoric acid modified kieselguhr, silica alumina and acid zeolites such as Zeolite B. Typical hydrocarbon feedstock materials for etherification reactions include olefinic streams, such as FCC light naphtha and butenes rich in iso-olefins. These aliphatic streams are produced in petroleum refineries by catalytic cracking of gas oil or the like.

The major reaction units are operatively connected in a synergistic combination whereby etherification reaction effluent is utilized to provide reactive olefins for zeolite catalyzed conversion in conjunction with olefin interconversion products. Isomerization, oligomerization, alkylation and aromatizations reactions may be controlled in the acidic zeolite catalysis zone to obtain a desirable distribution of normally liquid hydrocarbons useful in making gasoline and/or distillate range fuels or aromatics such as BTX for petrochemical feedstock. Advantageously, at least a portion of the gasoline range hydrocarbons are recovered with $C_5+$ etherate octane enhancers useful in quality motor fuels. MTBE and TAME are preferred ethers. The $C_4-C_6$ alkene fraction from the olefin interconversion zone is utilized as etherification feedstock, optionally with fresh feedstock rich in $C_4-C_6$ iso-olefins.

The reaction of methanol with iso-butylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, Dec. 1977. An article entitled "MTBE and TAME —A Good Octane Boosting Combo," by J.D. Chase, et al., *The Oil and Gas Journal*, Apr. 9, 1979, pages 149 -152, discusses the technology. A preferred catalyst is a bifunctional ion exchange resin which etherifies and isomerizes the reactant streams. A typical acid catalyst is Amberlyst 15 sulfonic acid resin.

MTBE and TAME are known to be high octane ethers. The article by J.D. Chase, et al., *Oil and Gas Journal*, Apr. 9, 1979, discusses the advantages one can achieve by using these materials to enhance gasoline octane. The octane blending number of MTBE when 10% is added to a base fuel $(R+O=91)$ is about 120. For a fuel with a low motor rating $(M+O=83)$ octane, the blending value of MTBE at the 10% level is about 103. On the other hand, for an $(R+O)$ of 95 octane fuel, the blending value of 10% MTBE is about 114.

Processes for producing and recovering MTBE and other methyl tertiary alkyl ethers from $C_4-C_7$ isoolefins are known to those skilled in the art, such as disclosed in U.S. Pat. No. 4,544,776 (Osterburg, et al.) and 4,603,225 (Colaianne et al.). Various suitable extraction and distillation techniques are known for recovering ether and hydrocarbon streams from etherification effluent.

Operating details for typical MOGD units are disclosed in U.S. Pat. Nos. 4,456,779; 4,497,968 (Owen et al.) and 4,433,185 (Tabak), incorporated herein by reference.

In the process for catalytic conversion of oxygenate and/or olefins to heavier hydrocarbons by catalytic oligomerization using an acid crystalline zeolite, such as ZSM-5 type catalyst, process conditions can be varied to favor the formation of either gasoline, distillate, lube range products or aromatics. In the aforenoted MOGD process, light olefins are oligomerized to high molecular weight distillate range olefins over ZSM-5. In that process olefin molecular weight growth through a sequence of oligomerization and cracking reactions is thermodynamically forced at relatively high pressures of about 5600 kPa (800 psia) and relatively low temperatures of about 260° C. (500° F.). At much lower pressure and higher temperature, thermodynamics restrict the olefin distribution to low molecular weight. This is the basis for the olefin interconversion process, i.e., to operate under conditions where lower olefins, such as $C_2$–$C_4$ olefins can be converted to an equilibrium distribution of olefins with iso-butenes and iso-pentenes maximized. The olefin interconversion process as utilized in the present invention can use fixed bed, moving bed or fluid bed reactors containing zeolite type catalysts such as ZSM-5. Operating conditions encompass temperatures between 200 and 400 C and low pressures, generally between 100 and 1500 kPa.

Optionally, conversion condition in the present invention may be controlled to favor the formation of aromatics, typified by the process known as M-2 Forming. Light aliphatic, paraffinic/olefinic feed can be converted under conditions described in U.S. Pat. No. 3,760,0242 to Cattanach, incorporated herein by reference. The operating conditions are temperatures from 300 to 750 C. and pressures from atmospheric to 3600 KPa (500 psig), preferably about 550 degrees C and 350 kPa. The reaction products comprise an effluent stream of light gases such as hydrogen and methane, unconverted light hydrocarbons and $C_{5+}$ aromatics.

The conversion of methanol, methanol equivalent, olefins and paraffins to gasoline, alkylated aromatics, and aromatics occurs under a broad range of operating conditions, but is preferably catalyzed by a crystalline-zeolite catalyst having acidic functionality. The preferred class of catalysts is characterized by a Constraint Index of 1 to 12 and a silica:alumina ratio of at least 12:1 and preferably higher e.g. 30:1, 70:1, 500:1, 1600:1 or even higher. As described in U.S. Pat. No. 3,998,889, the Constraint Index of a zeolite is a convenient measure of the extent to which a zeolite provides constrained access to its internal structure for molecules of different sizes. It is therefore a characteristic of the structure of the zeolite but is measured by a test which relies upon the possession of cracking activity by the zeolite. The sample of zeolite selected for determination of the Constrain Index of a zeolite should therefore represent the structure of the zeolite (manifested by its X-ray diffraction pattern) and have adequate cracking activity for the Index to be determined. If the cracking activity of the selected zeolite is too low, the Constraint Index may be determined by using a zeolite sample of the same structure but higher cracking activity which may be obtained, for example, by using an aluminosilicate zeolite of higher aluminum content. Details of the method of determining Constraint Index and of the values of the Index for typical zeolites are given in U.S. Pat. No. 3,998,899 to which reference is made for such details and other information in this respect.

The silica-alumina ratios referred to in this specification are the structural or framework ratios, that is, the ratio for the $SiO_4$ to the $AlO_4$ tetrahedra which together constitute the structure of which the zeolite is composed. This ratio may vary from the silica:alumina ratio determined by various physical and chemical methods. For example, a gross chemical analysis may include aluminum which is present in the form of cations associated with the acidic sites on the zeolite, thereby giving a low silica:alumina ratio. Similarly, if the ratio is determined by thermogravimetric analysis (TGA) of ammonia desorption, a low ammonia titration may be obtained if cationic aluminum prevents exchange of the ammonium ions onto the acidic sites. These disparities are particularly troublesome when certain treatments such as dealuminization methods which result in the presence of ionic aluminum free of the zeolite structure are employed to make highly siliceous zeolites. Due care should therefore be taken to ensure that the framework silica: alumina ratio is correctly determined.

Preferred zeolites which have the specified values of Constraint Index and silica:alumina ratio include zeolites ZSM-5, ZSM-11, ZSM-12, ZSM-35, ZSM-38 and ZSM-48, which are described in U.S. Pat. Nos. 3,702,886 (ZSM-5), 3,709,979 (ZSM-11), 3,832,449 (ZSM-12), 4,076,842 (ZSM-23) and 4,016,245 (ZSM-35), 4,046,859 (ZSM-38) and European Patent Publication No. 15132, and reference is made to these patents for details of these zeolites, their preparation and properties. Of these zeolites, ZSM-5 is preferred.

The zeolite catalyst used is at least partly in the hydrogen form e.g. HZSM-5 but other cations e.g. rare earth cations may also be present. When the zeolites are prepared in the presence of organic cations, they may be quite inactive possibly because the intracrystalline free space is occupied by the organic cations from the forming solution. The zeolite may be activated by heating in an inert atmosphere to remove the organic cations e.g. by heating at over 500 degrees C. for 1 hour or more. The hydrogen form can then be obtained by base exchange with ammonium salts followed by calcination e.g. at 500 degrees C. in air. Other cations, e.g. metal cations, such as Ga, Zn, Cu, Pt and Fe, can be introduced by conventional base exchange techniques.

Referring to FIG. 1, in the process of the instant invention, hydrocarbon stream 100 rich in $C_2$ + normal olefins is passed to an olefins interconversion zone containing acidic catalyst, preferrably ZSM-5 or crystalline silicoaluminophosphate of intermediate pore size, for the conversion of lower olefins to higher olefins rich in $C_4$–$C_6$ iso-olefins plus $C_{7+}$ olefinic gasoline and unconverted hydrocarbons. The $C_4$–$C_6$ stream 111 is passed to etherification zone together with a fresh iso-olefin $C_4$–$C_6$ stream 113 and methanol stream 114. The etherification zone effluent 116 is cooled in exchanger 117 and passed to debutanizer or depentanizer 118 where a hydrocarbon stream 119 rich in $C_5$ + ethers is separated and an overhead stream 120 containing unreacted methanol and olefins. The overhead stream, in conjunction with $C_{7+}$ olefinic stream 121 from interconversion zone 115 and, optionally, unreacted olefins containing interconversion light gas by-product from zone 115 are passed to oxygenates and olefins conversion zone 122 containing metallosilicate zeolite catalyst. Conversion zone 122 may be operated under oligomerization conditions and/or aromatizations conditions to convert methanol and olefins or olefins/paraffinsto higher hydrocarbons containing distillate or aromatics-rich hydrocarbons. Preferably, $C_5+$ gasoline boiling range hydrocarbons 123 are produced rich in aromatics. Line 124 recovers $C_{4-}$ hydrocarbon products.

While the invention has been described by reference to specific embodiments, there is no intent to limit the invention except as described in the following claims.

What is claimed is:

1. a process for producing liquid fuel mixtures from olefin feedstock and lower alcohols by multistage etherification, olefin interconversion and olilgomerization reactions, comprising the steps of:
   (a) contacting an olefinic hydrocarbon feedstock rich in $C_{2+}$ n-alkenes with acidic, medium pore metallosilicate particles in an olefin interconversion zone under mild olefin interconversion conditions between 200 and 400° C. whereby a first effluent stream comprising $C_4$-$C_6$ alkenes rich in isoalkenes, a second stream comprising $C_7+$ olefinic gasoline boiling range hydrocarbons and a third stream comprising unconverted hydrocarbons are produced;
   (b) reacting said first stream with lower aliphatic alcohol in the presence of an acid etherification catalyst under reaction conditions effective to produce a mixture of tertiary alkyl ethers;
   (c) recovering the resulting reaction effluent containing tertiary alkyl ethers, $C_5+$ gasoline range hydrocarbons, and a light hydrocarbon fraction containing unreacted alkenes and unreacted alcohol;
   (d) recovering said light hydrocarbon fraction containing said unreacted alkenes from the reaction effluent of step (c) along with said unreacted alcohol;
   (e) contacting the recovered light hydrocarbon containing alcohol fraction from step (d) and step (a) second and third stream with an acid oligomerization and oxygenate conversion catalyst to convert at least a portion of said unreacted alkenes and alcohol to heavier liquid hydrocarbon product, including $C_{10}+$ distillate range hydrocarbons, aromatics and or $C_5$-$C_9$ gasoline boiling range hydrocarbons.

2. The process of claim 1 wherein said iso-alkene includes iso-butene, said alcohol includes methanol, said oligomerization conversion catalyst comprises a shape selective medium pore acid metallosilicate zeolite and said tertiary alkyl ethers contain methyl t-butyl ether.

3. The process of claim 1 wherein the tertiary alkyl ethers are recovered from the reaction effluent of step (c) in a product stream comprising $C_5+$ gasoline range hydrocarbons.

4. The process of claim 3 wherein the tertiary alkyl ethers comprise $C_5$ to $C_8$ methyl tertiaryalkyl ethers.

5. The process of claim 3 wherein said olefinic feedstock rich in $C_2+$n-alkenes is rich in butenes.

6. The process of claim 3 wherein the said olefinic feed stock rich in $C_2+$n-alkenes contains about 10 to 50 weight percent isobutylene.

7. The process of claim 1 wherein said alcohol comprises methanol wherein the light hydrocarbon stream containing said unreacted alcohol in step (d) is recovered by fractionating substantially the entire etherification reaction effluent in a depentanizer or debutanizer column, said light hydrocarbon containing an overhead vapor stream right in $C_{5-}$ or $C_{4-}$ lower olefin and a minor amount of unreacted methanol, and the resulting liquid product stream comprising $C_5+$ or $C_6+$ liquid hydrocarbon and $C_5+$ methyl tertiary alkyl ether.

8. The process of claim 1 wherein the etherification catalyst comprises an acid sulfonic acid resin solid.

9. The process of claim 1 wherein the etherification conditions comprise a high stoichiometric excess amount of said lower aliphatic alcohol over said isoalkenes to shift the equilibrium of the etherification reaction substantially toward the formation of $C_5+$ teritiary alkyl ethers.

10. The process of claim 9 wherein the mole ratio of said lower aliphatic alcohol to $C_4+$ isoalkenes is between 10:1 and 1:1.

11. The process of claim 8 wherein the mole ratio of said lower aliphatic alcohol to $C_4+$ isoalkenes is about 1.2:1.

12. The process of claim 1 wherein said acidic, metalloislicate of said olefins interconversion zone has the structure of ZSm-5.

13. The process of claim 1 wherein step (a) unconverted hydrocarbons comprise paraffins, wherein said paraffins are converted to aromatics in step (e).

* * * * *

UNITED STATES PATENT AND TRADEMARK OFFICE
CERTIFICATE OF CORRECTION

PATENT NO. : 4,886,925
DATED : December 12, 1989
INVENTOR(S) : Mohsen N. Harandi It is certified that error appears in the above-identified patent and that said Letters Patent is hereby corrected as shown below:

On the title page:

[73] Assignee: Mobil Oil Corporation, New York, NY

Signed and Sealed this

Twenty-ninth Day of January, 1991

Attest:

HARRY F. MANBECK, JR.

*Attesting Officer*     *Commissioner of Patents and Trademarks*